US007595390B2

(12) United States Patent
Moussa et al.

(10) Patent No.: US 7,595,390 B2
(45) Date of Patent: Sep. 29, 2009

(54) INDUSTRIALLY SCALABLE NUCLEOSIDE SYNTHESIS

(75) Inventors: Adel Moussa, Burlington, MA (US); Jing Yang Wang, Acton, MA (US); Richard Storer, Folkestone (GB)

(73) Assignee: Novartis AG, Basel (CH)

( * ) Notice: Subject to any disclaimer, the term of this patent is extended or adjusted under 35 U.S.C. 154(b) by 377 days.

(21) Appl. No.: 10/833,925

(22) Filed: Apr. 28, 2004

(65) Prior Publication Data
US 2005/0004357 A1 Jan. 6, 2005

Related U.S. Application Data

(60) Provisional application No. 60/466,196, filed on Apr. 28, 2003.

(51) Int. Cl.
C07H 19/073 (2006.01)
(52) U.S. Cl. ............... 536/27.11; 536/28.5; 536/28.54
(58) Field of Classification Search ............ 536/27.11, 536/28.5
See application file for complete search history.

(56) References Cited

U.S. PATENT DOCUMENTS

| | | | |
|---|---|---|---|
| 3,116,282 | A | 12/1963 | Hunter |
| 3,891,623 | A | 6/1975 | Vorbrüggen et al. |
| 4,209,613 | A | 6/1980 | Vorbrüggen |
| 4,622,339 | A | 11/1986 | Lieb et al. |
| 4,689,404 | A | 8/1987 | Kawada et al. |
| 4,754,026 | A | 6/1988 | Kawada et al. |
| 4,914,233 | A | 4/1990 | Freskos et al. |
| 4,957,924 | A | 9/1990 | Beauchamp |
| 5,200,514 | A | 4/1993 | Chu |
| 5,212,293 | A | 5/1993 | Green et al. |
| 5,414,078 | A | 5/1995 | Liotta et al. |
| 5,559,101 | A * | 9/1996 | Weis et al. ............... 514/45 |
| 5,596,087 | A | 1/1997 | Alla et al. |
| 5,750,676 | A | 5/1998 | Vorbrüggen et al. |
| 5,760,208 | A | 6/1998 | Abushanab et al. |
| 6,348,587 | B1 | 2/2002 | Schinazi et al. |
| 6,369,040 | B1 | 4/2002 | Acevedo et al. |
| 6,395,716 | B1 | 5/2002 | Gosselin et al. |
| 6,444,652 | B1 | 9/2002 | Gosselin et al. |
| 6,566,344 | B1 | 5/2003 | Gosselin et al. |
| 6,569,837 | B1 | 5/2003 | Gosselin et al. |
| 6,596,859 | B1 | 7/2003 | Abushanab et al. |
| 2003/0083306 | A1 | 5/2003 | Imbach et al. |
| 2004/0181051 | A1* | 9/2004 | Storer et al. ............... 536/27.1 |
| 2004/0266996 | A1 | 12/2004 | Rabi |

FOREIGN PATENT DOCUMENTS

| | | |
|---|---|---|
| DE | 1 919 307 A1 | 1/1971 |
| DE | 25 08 312 A1 | 9/1976 |
| DE | 140 254 Z | 2/1980 |
| DE | 21 22 991 C2 | 6/1982 |
| DE | 42 24 737 A1 | 2/1994 |
| DE | 100 20 275 | 10/2001 |
| EP | 0 351 126 | 1/1990 |
| EP | 0 352 248 A1 | 1/1990 |
| EP | 0 683 171 | 11/1995 |
| EP | 1 348 712 | 10/2003 |
| GB | 1 542 442 | 3/1979 |
| GB | 1542442 A | 3/1979 |
| JP | 46 21872 | 6/1971 |
| JP | 56 49398 | 5/1981 |
| JP | 61-263995 A2 | 11/1986 |
| JP | 63 26183 | 2/1988 |
| JP | 06-135988 | 5/1994 |
| JP | 06-293645 A | 10/1994 |
| JP | 09-059292 A | 3/1997 |
| WO | WO 92/18517 A1 | 10/1992 |
| WO | WO 95/07287 A1 | 3/1995 |
| WO | WO 96/11204 A1 | 4/1996 |
| WO | WO 96/13512 A2 | 5/1996 |
| WO | WO 96/40164 A1 | 12/1996 |
| WO | WO 00/09531 A2 | 2/2000 |
| WO | 2001/072698 | 10/2001 |
| WO | WO 01/96353 A2 | 12/2001 |
| WO | 2002/44194 | 6/2002 |
| WO | 2003/087118 | 10/2003 |

OTHER PUBLICATIONS

[R] Spardari et al., "L-Thymidine Is Phosphorylated by Herpes Simplex Virus Type 1 Thymidine Kinase and Inhibits Viral Growth," Journal of Medicinal Chemistry, 35(22), 4214-4220 (1992).*
(S) Robins et al., "Purine Nucleosides XXIX. The Synthesis of 2'-Deoxy-L-adenosine and 2'-Deoxy-L-guanosine and Their[alpha] Anomers," Journal of Organic Chemistry, 35(3), 636-639 (Mar. 1970).*
(T) Fujimori et al., "A Convenient and Stereoselective Synthesis of 2'-Deoxy-[beta]-L-nucleosides," Nucleosides & Nucleotides, 11(2-4), 341-349 (1992); only CAPLUS abstract supplied.*
(U) McCormick et al., "Structure and Total Synthesis of HF-7, a Neuroactive Glyconucleoside Disulfate from the Funnel-Web Spider *Holena curta*," J. American Chemical Society, 121(24), 5661-5665 (1999); web published Jun. 6, 1999.*
[R] Spardari et al., "L-Thymidine Is Phosphorylated by Herpes Simplex Virus Type 1 Thymidine Kinase and Inhibits Viral Growth," Journal of Medicinal Chemistry, 35(22), 4214-4220 (1992).*
(S) Robins et al., "Purine Nucleosides. XXIX. The Synthesis of 2'-Deoxy-L-adenosine and 2'-Deoxy-L-guanosine and Their [alpha] Anomers," Journal of Organic Chemistry, 35(3), 636-639 (Mar. 1970).*

(Continued)

*Primary Examiner*—Lawrence E. Crane
(74) *Attorney, Agent, or Firm*—Leslie Fischer

(57) ABSTRACT

An industrially scalable two-step process for preparing a β-L-2'-deoxy-nucleoside that results in a predominance of the β- over the α-anomeric form of the compound is described. An optional third step may be used to prepare 3'-prodrugs of desirable β-L-2'-deoxy-nucleosides for the delivery of these pharmaceuticals effective for treating viral diseases. The synthetic process is applicable in particular to the formation of β-L-2'-deoxy-cytidine, a pharmaceutically acceptable salt or prodrug thereof. The process can provide a relatively uncontaminated product that may require no further isolation or purification, thereby making the synthesis easily scalable for industrial manufacture.

23 Claims, 9 Drawing Sheets

OTHER PUBLICATIONS (T) Fujimori et al., "A Convenient and Stereoselective Synthesis of 2'-Deoxy-[beta]-L-neucleosides," *Nucleosides & Neucleotides*, 11(2-4), 341-349 (1992).*
(U) McCormick et al., "Structure and Total Synthesis of HF-7, a Neuroactive Glyconucleoside Disulfate for the Funnel-Web Spider *Holena curta*," J. American Chemical Society, 121(24), 5661-5665 (1999); web published Jun. 6, 1999.*
(V) Hoffer, M., "[alpha]-Thymidin," Chemische Berichte, 95, 2777-2781 (1960).*
Bloch, A. et al. "The Role Of The 5'-Hydroxyl Group of Adenosine In Determining Substrate Specificity For Adenosine Deaminase," *J. Med. Chem.*, 10(5):908-12 (Sep. 1967).
Davisson, V.J., et al., "Synthesis of Nucleotide 5'-Diphosphates from 5'-O-Tosyl Nucleosides," *J. Org. Chem.*, 52(9):1794-1801 (1987).
Fox, J.J. et al., "Thiolation of nucleosides. II. Synthesis of 5-methyl-2'-deoxycytidine and related pyrimidine nucleosides," *J. Am. Chem. Soc.*, 81:178-187 (Jan. 5, 1959).
Furukawa, Y., et al, "A novel method for the synthesis of purine nucleosides using Friedel-Crafts catalysts," *Chem. Pharm. Bull.*, 16(6):1076-1080 (Jun. 1968).
Hoard, D.E., et al., "Conversion of Mono- and Oligodeoxyribonucleotides to 5'-Triphosphates," *J. Am. Chem. Soc.*, 87(8):1785-1788 (Apr. 20, 1965).
Holy, A., "Nucleic Acid Components and Their Analogs. CLIII. Preparation of 2'-deoxy-L-Ribonucleosides of the Pyrimidine Series," *Collect. Czech. Chem. Commun.*, 37(12):4072-4087(1972).
Imai, K., et al., "Studies on Phosphorylation. IV. Selective Phosphorylation of the Primary Hydroxyl Group in Nucleosides." *J. Org. Chem.*, 34(6):1547-1550 (Jun. 1969).
Kamaike, K., et al., "An efficient method for the synthesis of [4-$^{15}$N]cytidine, 2'-deoxy[4-$^{15}$N]cytidine, [6-$^{15}$N]adenosine, and 2'-deoxy [6-$^{15}$N]adenosine derivatives," *Nucleosides and Nucleotides*, 15(1-3):749-769 (1996).
Kaneko, M., et al., "A convenient synthesis of cytosine nucleosides," *Chem. Pharm. Bull.*, 20:1050-1053 (1972).
Lin, T.-S., et al., "Synthesis of Several Pyrimidine L-Nucleoside Analogues as Potential Antiviral Agents," *Tetrahedron Letters*, 51(4):1055-1068 (1995).
Maga, Giovanni, et al., "Lack of stereospecificity if suid pseudorabies virus thymidine kinase," *Biochem. J.*, 294(2):381-385 (1993).
Saladino, R., et al., "A new and efficient synthesis of cytidine and adenosine derivatives by dimethyldioxirane oxidation of thiopyrimidine and thiopurine nucleosides," *J. Chem. Soc., Perkin Trans. I*, 21:3053-3054 (1994).
Tyrsted, G., et al. "Inhibition of the synthesis of 5-phosphoribosyl-l-pyrophosphate by 3'-deoxy-adenosine and structurally related nucleoside analogs." *Biochim. Biophys. Acta*, 155(2):619-622 (Feb. 26, 1968).
Verri, A., et al., "Lack of enantiospecificity of human 2'-deoxycytidine kinase: relevance for the activetion of β-L-deoxycytidine analogs as antineoplastic and antiviral agents," *Molecular Pharmacology*, 51(1):132-138 (Jan. 1997).
Verri, A., et al., "Relaxed Enantioselectivity of Human Mitochondrial Thymidine Kinase and Chemotherapeutic Uses of L-Nucleoside Analogues," *Biochem. J.*, 328(1):317-320 (Nov. 15, 1997).
Von Janta-Lipinski, M., et al., "Newly Synthesized L-Enantiomers of 3'-Fluoro-Modified β-2'-Deoxyribonucleosides 5'-Triphosphates Inhibit Hepatitis B DNA Polymerase but not the Five Cellular DNA Polymerases α, β, γ, δ, and ε Nor HIV-1 Reverse Transcriptase," *J. Medicinal Chemistry*, 41(12):2040-2046 (May 21, 1998).
Aoyama et al., (1996) *Nucleosides & Nucleotides*, 15(1-3): 733-738.
Asakura et al., (1990) *J. Org. Chem.* 55: 4928-4933.
Asakuyra et al., (1988) *Tetrahedron Lett.* 29(23): 2855-2858.
Bock et al., (1984) *Acta Chem. Scand. B.*, 38: 555-561.
Bock et al., (1981) *Carbohydr. Res.*, 90: 17-26.
Bock et al., (1982) *Carbohydr. Res.*, 104: 79-85.
Bock et al., (1979) *Carbohydr. Res.*, 68: 313-319.
Codington et al., (1963) *J. Org. Chem.*, 29: 558-564.
Du et al., (1999) *Nucleosides and Nucleotides*, 18(2): 187-195.
Englisch et al., (1991) *Angew. Chem.*, 30(6): 613-722.
Fraser et al., (1993) *J. Heterocycl. Chem.*, 30(5): 1277-1288.
Graf et al., (1993) *Liebigs Ann. Chem.*, 1091-1098.
Harada et al., (1981) *Chem. Lett.*, 1109-1110.
Hirota et al., (1993) *Synthesis*, 210: 213-215.
Holy et al., (1974) *Collect. Czech. Commun.*, 39: 3157-3167.
Humphlett, (1967) *Carbohydrate Research*, 4: 157-164.
Huryn et al., (1992) *Chem. Rev.* 92: 1745-1768.
Isbell, (1963) *Methods in Carbohydrate Research*, 2: 13-14.
Jung et al., (1997) *Tetrahedron Lett.*, 38(24): 4199-4202.
Jung et al., (1998) *Tetrahedron Letters*, 39: 4615-4618.
Liotta et al., (1992) *Tetrahedron Letters*, 33(47): 7083-7086.
Lundt et al., (2001) *Topics in Currant Chemistry*, 215: 177-191.
Manfredini et al., (2001) *Bioorg. Med. Chem. Letters*, 11: 1329-1332.
Moyroud et al., (1999) *Tetrahedron* 55: 1277-1284.
Kita et al., Chemistry of O-Silylated Ketene Acetals: Stereocontrolled Synthesis of 2-Deoxy- and 2-Deoxy-2-C-alkylerythyro-pentoses: (1988), *J. Org. Chem.* 53, 554-561.
Escudier et al., "A Short Synthesis of Substituted β-Hydroxyγ-Butyrolactones and 2-Deoxyhexofruanosides", (1992), *Tetrahedron Letters* 33:11 1439-1442.
Walker et al. (1996) "A Facile, Multigram Synthesis of Ribofuranoid Glycals" *J. Org. Chem.* 61, 2219-2221.
Okabe et al., (1991) *J. Org. Chem.*, 56(14): 4392-4397.
Pragnacharyulu et al., (1995) *J. Org. Chem.* 60: 3096-3099.
Pratt et al., (1952) *J. Am. Chem. Soc.*, 74: 2200-2205.
Rao et al., (1994) *J. Chem. Soc Comm.*, 1255-1256.
Ravid et al., (1978) *Tetrahedron*, 34: 1449-1452.
Recondo et al., (1959) *Helv. Chim. Acta.*, 121: 1171-1173.
Sawai et al., (1994) *Nucleosides & Nucleotides*, 13(6-7): 1647-1654.
Sawai et al., (1994) *Chem. Lett.*, 605-606.
Schinazi et al., (1979) *J. Med. Chem.*, 22 (10): 1273-1277.
Shull et al., (1996) *J. Carbohydr. Chem.*, 15: 955-964.
Stick et al., (2002) *Aust. J. Chem.*, 55: 83-85.
Sznaidman et al., (2002) *Nucleosides, Nucleotides & Nucleic Acids*, 21(2): 155-163.
Takahata et al., (1994) *J. Org. Chem.*, 59: 7201-7208.
Taniguchi et al., (1974) *Tetrahedron*, 30: 3547-3552.
Tronchet et al., (1990) *Tetrahedron Lett.*, 31(4): 531-534.
Urata et al., (1992) *Nucleic Acids Res.*, 20(13): 3325-3332.
Wang et al., (2001) *Nucleosides, Nucleotides & Nucleic Acids*, 20: 11-40.
Yadav et al., (2002) *Tetrahedron Letters*, 43: 3837-3839.
Zhang et al., (1999) *Nucleosides and Nucleotides*, 18(11): 2357-2365.
Zinchenko, (1989) *Khimiya Prirodnykh Soedinenii*, 4: 587-588.

* cited by examiner

Synthesis of 2'-Deoxy-β-L-Cytidine (β-LdC)

Synthesis of BOC 3'-O-Val-LdC

Figure 3

Synthesis of LdC from Chloro-Sugar Using Silylated Cytosine

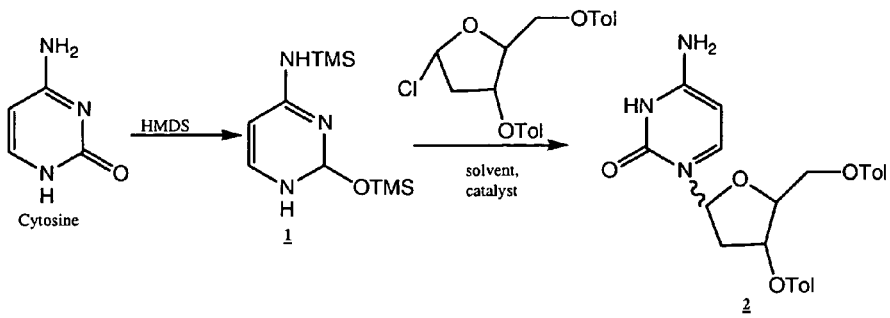

| Conditions | | | Results | |
|---|---|---|---|---|
| Solvent | Catalyst | Temp/Time | Yield | α:β ratio |
| $CHCl_3$ | | r.t./overnight | 93 % | 1.3 : 1 |
| $CH_3CN$ | | r.t./overnight | 70 % | 2.3 : 1 |
| THF | | r.t./overnight | 94 % | 2.2 : 1 |
| $CHCl_3$ | TMSOTf (1.5 eq.) | r.t./30 min. | 80 % | 1.4 : 1 |
| $CH_3CN$ | TMSOTf (1.5 eq.) | r.t /30 min. | Reaction produced several by-products | |
| DCE | | 65 °C/4 hours | | 2 : 1 |
| $CH_3CN$ | | 65 °C/2 hours | | 2 : 1 |
| CHCl3 | $SnCl_4$(1.5 eq) | r.t/overnight | | 1 : 1.1 |
| $CH_3CN$ | $SnCl_4$(1.5 eq) | r.t/overnight | | 2.1 : 1 |
| DCE | $SnCl_4$(1.5 eq) | r.t/overnight | Reaction produced several by-products | |
| Toluene | $SnCl_4$(1.5 eq) | r.t/overnight | | 1.4 : 1 |

Synthesis of LdC from Chloro-Sugar Using Silylated Benzoylcytosine

* No catalyst used

| Solvent | Temp/Time | α:β ratio |
|---|---|---|
| CH₃CN | r.t / overnight | 1.8 : 1 |
| DCE | r.t / overnight then 50 °C / 4 hours | 1.2 : 1 |

Figure 5

Synthesis of LdC from Chloro-Sugar Using $N^4$-Benzoylcytosine

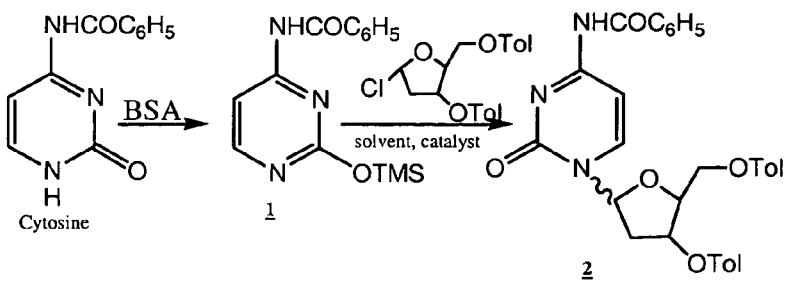

| Equivalent (1) | Cl-sugar mmol | Solvent | Catalyst, Eq. | Temp., Time | α:β ratio |
|---|---|---|---|---|---|
| 1.3 | 1.5 | CHCl₃ | SnCl₄, 1.3 | r.t., 30 min. | 1:2.0 |
| 1.3 | 1.5 | CH₃CN | SnCl₄, 1.3 | 0 °C-r.t., 1hr | 1:1.6 |
| 1.3 | 1.5 | DCE | SnCl₄, 1.3 | 0 °C-r.t., 1hr | 1:2.16 |
| 1.3 | 1.5 | CHCl₃ | SnCl₄, 2.2 | 0 °C-r.t., 1hr | 1:1.7 |
| 1.3 | 1.5 | CHCl₃ | SnCl₄, 2.2 | 0 °C-r.t., 1hr | 1:1.7 |
| 1.3 | 3.0 | CH₂Cl₂ | SnCl₄, 2.0 | r.t., 1hr | 1:1.95 |
| 1.3 | 3.0 | CH₂Cl₂ | TiCl₄, 2.0 | r.t., 1hr | 1:2.36 |
| 1.3 | 3.0 | THF | TiCl₄, 2.0 | r.t., 1hr | 1:1.4 |
| 1.3 | 1.5 | CHCl₃ | - | r.t., 2.5hr. | 1:1.6 |
| 1.3 | 3.0 | CH₂Cl₂ | SnCl₄, 0.085 | r.t., 30 min. | 1:1.2 |
| 1.3 | 3.0 | CHCl₃ | CuI, 1.0 | r.t., 30 min. | 1:1.5 |
| 1.2. | 1.67 | CHCl₃ | SnCl₂, 1.0 | r.t., overnight | 1:1.2 |
| 1.2 | 1.67 | CHCl₃ | CuI (1.0) SnCl₄ (0.15) | r.t., overnight | 1:1.4 |
| 1.3 | 1.5 | CHCl₃ | SnCl₄, 0.5 | 50 °C, 1.5 hr | 1:1.5 |

Coupling Reactions of Silylated Cytosine with Cl-Sugar

| Equivalent (1) | Cl-Sugar mmol | Solvent | Catalyst/ Equivalent | Temp/ Time | α:β ratio |
|---|---|---|---|---|---|
| 2.0 | 0.67 | CHCl$_3$ | SnCl4 1.5 | r.t. 1hr | 1.05:1.0 |
| 2.0 | 0.67 | CHCl$_3$ | - | r.t. 2hr | 1:1.1 |
| 2.0 | 0.671 | CHCl$_3$ | CuI/py (1.0/0.5) | r.t. 1hr. | 1:1.4 |

Figure 7

Coupling Reactions Using $N^4$-Benzoylcytosine

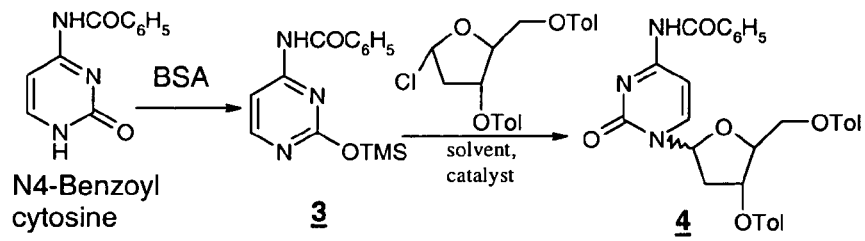

| Eq. (3) | Cl-Sugar mmol | Solvent | Catalyst/ Equivalent | Temp/ Time | α:β ratio Product 4 |
|---|---|---|---|---|---|
| 2.0 | 0.67 | CHCl$_3$ | CuI/py (1.0/0.5) | r.t | complex. mixture |
| 2.0 | 0.67 | CHCl$_3$ | CuI/py (1.0/0.5) | 40°C | 1:1.2 |
| 2.0 | 0.67 | CHCl$_3$ | CuI/py (1.0/0.5) | r.t., 1.5 hr | 1:1.25 |
| 2.0 | 0.67 | CH2Cl$_2$ | CuI/py (1.0/0.5) | r.t., 0.5hr | 1:2.1 |
| 2.0 | 0.67 | CH$_2$Cl$_2$ | CuI/py (1.0/0.5) | 40°C | 1:2.0 |
| 2.0 | 0.67 | CH$_2$Cl$_2$ | CuI/py (1.0/0.5) | r.t., 0.5 hr | 1:1.72 |
| 2.0 | 0.5 | CH$_2$Cl$_2$ | CuI/py (1.0/0.5) | 40°C, 1 hr | 1:1.8 |
| 4.0 | 0.25 | CH$_2$Cl$_2$ | CuI/py (1.0/0.5) | r.t., 1hr. | 1:2.65 |
| 2.0 | 0.5 | CH$_2$Cl$_2$ | py, 0.5 | r.t., 1 hr | 1.93:1 |
| 1.3 | 3.0 | CH$_2$Cl$_2$ | BF$_3$, 0.5 | r.t., 1hr | 1:1.3 |
| 6.0 | 0.5 | CH$_2$Cl$_2$ | CuI/py (1.0/0.5) | r.t., 1hr. | 1:2.9 |
| 4.0 | 0.5 | CH$_2$Cl$_2$ | CuI, 1.0 | r.t., 1hr. | 1:3.0 |
| 4.0 | 1.5 | CH$_2$Cl$_2$ | CuI, 1.0 | r.t., 1hr. | 1:2.7 |
| 4.0 | 1.0 | CH$_3$Cl | CuI, 1.0 | r.t., 0.75hr. | 1:1.9 |
| 4.0 | 1.0 | CH$_3$Cl | CuI, 1.0 | r.t., 1hr. | 1:1.95 |

FIGURE 8

Reaction Results Using TiCl$_4$ as a Catalyst

| 3 Equivalents | Conc. of 3 in DCM | TiCl$_4$ Equivalents | Temp | α:β ratio |
|---|---|---|---|---|
| 2.0 | 0.17M | 2.0 | r.t. | 1:1.5 |
| 2.0 | 0.17M | 2.0 | 40°C | 1:1.2 |
| 4.0 | 0.17M | 2.0 | r.t. | 1:2.2 |
| 1.3 | 0.2M | 2.0 | r.t. | 1 : 2.4 |
| 1.3 | 0.2M | 2.0 | 0-5°C | 1 : 2.65 |
| 1.3 | 0.2M | 3.0 | r.t. | 1 : 3.4 |
| 1.3 | 0.2M | 3.0 | 0-5°C | 1 : 3.5 |
| 1.3 | 0.1M | 3.0 | 0-5°C | 1 : 3.45 |
| 1.3 | 0.2M | 4.0 | 0-5°C | 1 : 3.8 |
| 1.3 | 0.4M | 4.0 | 0-5°C | 1 : 3.2 |
| 2.0 | 0.2M | 4.0 | 0-5°C | 1 : 3.2 |
| 2.0 | 0.2M | 6.0 | 0-5°C | 1 : 4.8 |
| 1.3 | 0.2M | 8.0 | 0-5°C | 1 : 5.49 |
| 1.3 | 0.2M | 10.0 | 0-5°C | 1 : 5.52 |
| 2.5 | 0.2M | 10.0 | 0-5°C | 1 : 5.62 |

Where 3 refers to N$^4$-benzoyl-2-silyl-cytosine depicted in Figure 7.

Coupling Reactions Using 3,4-Dimethoxybenzoylcytosine 3,4-dimethoxybenzoyl cytosine

| Silylated base Eq. | Cl-Sugar mmol | Solvent/ ml | Catalyst/ Equivalent | Temp/ Time | α:β ratio |
|---|---|---|---|---|---|
| 1.3 | 0.75 | CH$_2$Cl$_2$ | TiCl$_4$ 2.0 | r.t./0.75hr | 1:2.5 |
| 1.3 | 0.75 | CH$_2$Cl$_2$ | SnCl$_4$ 2.0 | r.t./0.75hr | 1:1.6 |
| 4.0 | 0.49 | CH$_2$Cl$_2$ | CuI/py 1.0/0.5 | r.t./0.75hr | 1:2.3 |

US 7,595,390 B2

INDUSTRIALLY SCALABLE NUCLEOSIDE SYNTHESIS

CROSS-REFERENCE OF THE INVENTION

This application claims priority to U.S. Provisional Application No. 60/466,196, filed Apr. 28, 2003, which is incorporated by reference.

FIELD OF THE INVENTION

The field of the invention is that of nucleoside synthesis scalable for production at industrial levels, and that of β-L-2'-deoxycytidine in particular. β-L-2'-deoxycytidine is important as an antiviral agent and also an intermediate in the synthesis of pharmaceutical compounds and compositions.

BACKGROUND OF THE INVENTION

Infections of Hepatitis B virus (HBV) exist at epidemic levels worldwide. Following an incubation period of from about two to six months during which the host is unaware of the infection, HBV can lead to acute hepatitis and liver damage that cause abdominal pain, elevated blood levels of certain enzymes, and jaundice. It may also cause fulminant hepatitis, a rapidly progressive and often fatal form of the disease in which massive sections of the liver are destroyed.

Patients generally recover from acute hepatitis. However, some patients experience a persistence of high levels of viral antigen in their blood for an extended, indefinite period of time that results in a chronic infection. Such chronic infections lead to chronic persistent hepatitis, which is most commonly found in developing countries. By mid-1991, there were approximately 225 million chronic HBV carriers in Asia alone, and nearly 300 million carriers worldwide. Chronic persistent hepatitis is characterized by any one or more of the following symptoms: fatigue, cirrhosis of the liver, and hepatocellular carcinoma, a primary liver cancer.

In western, industrialized countries, groups at high risk for HBV infection include those in contact with HBV carriers or their blood samples. The epidemiology of HBV is similar to that of acquired immune deficiency syndrome (AIDS), which accounts for the common finding of HBV infection in patients with AIDS or AIDS-related complex. However, HBV is more contagious than HIV.

Within the past few years, vaccines have been produced successfully through genetic engineering. These vaccines are used widely, but cannot help those already infected with HBV. Daily treatments with genetically produced α-interferon also show promise, but are successful in only about one-third of the patients who receive it. Another drawback to the use of interferon is that it cannot be given orally.

A number of synthetic nucleosides have been identified that exhibit activity against HBV. The (−)-enantiomer of BCH-189 (2',3'-dideoxy-3'-thiacytidine), known as 3TC, has been approved for the treatment of hepatitis B. See U.S. Pat. No. 5,532,246 as well as EPA 0 494 119 A1 filed by BioChem Pharma, Inc.

Adefovir (9-{2-(phosphonomethoxy)ethyl}adenine, also referred to as PMEA or ({2-(6-amino-9H-purin-9-yl) ethoxy}methylphosphonic acid), also has been approved in the United States for the treatment of patients infected with hepatitis B virus. See, for example, U.S. Pat. Nos. 5,641,763 and 5,142,051. Resistance to adefovir treatment in patients with HBV has been noted.

β-2-Hydroxymethyl-5-(5-fluorocytosin-1-yl)-1,3-oxathiolane ("FTC"), claimed in U.S. Pat. Nos. 5,814,639; 5,914, 331 and 6,703,396 to Liotta et al., exhibits activity against HBV. See Furman et al., "The Anti-Hepatitis B Virus Activities, Cytotoxicities, and Anabolic Profiles of the (−) and (+) Enantiomers of cis-5-Fluoro-1-{2-(Hydroxymethyl)-1,3-oxathiolane-5-yl}-Cytosine" Antimicrobial Agents and Chemotherapy, December 1992, 2686-2692; and Cheng, et al., Journal of Biological Chemistry, 1992, 267 (20), 13938-13942.

U.S. Pat. Nos. 5,565,438, 5,567,688 and 5,587,362 (Chu, et al.) disclose the use of 2'-fluoro-5-methyl-β-L-arabinofuranolyluridine (L-FMAU) for the treatment of hepatitis B and Epstein Barr virus.

Yale University and The University of Georgia Research Foundation, Inc. disclose the use of L-FDDC (5-fluoro-3'-thia-2',3'-dideoxycytidine) for the treatment of hepatitis B virus in WO 92/18517.

WO 96/40164 filed by Emory University, UAB Research Foundation, and the Centre National de la Recherche Scientifique (CNRS) discloses a number of β-L-2',3'-dideoxynucleosides for the treatment of hepatitis B.

WO 95/07287 also filed by Emory University, UAB Research Foundation, and the Centre National de la Recherche Scientifique (CNRS) discloses 2'- or 3'-deoxy and 2',3'-dideoxy-β-L-pentofuranosyl nucleosides for the treatment of HIV infection.

WO96/13512 filed by Genencor International, Inc., and Lipitek, Inc., discloses the preparation of L-ribofuranosyl nucleosides as antitumor agents and virucides.

WO95/32984 discloses lipid esters of nucleoside monophosphates as immuno-suppresive drugs.

DE 4224737 discloses cytosine nucleosides and their pharmaceutical uses.

Idenix Pharmaceuticals, Ltd. discloses 2'-deoxy-β-L-erythropentofurano-nucleosides, and their use in the treatment of HBV in U.S. Pat. Nos. 6,395,716; 6,444,652; 6,566,344 and 6,539,837. See also WO 00/09531. A method for the treatment of hepatitis B infection in humans and other host animals is disclosed that includes administering an effective amount of a biologically active 2'-deoxy-β-L-erythro-pentofuranonucleoside (alternatively referred to as β-L-dN or a β-L-2'-dN) or a pharmaceutically acceptable salt, ester or prodrug thereof, including β-L-deoxyribothymidine (β-L-dT), β-L-deoxyribocytidine (β-L-dC), β-L-deoxyribouridine (β-L-dU), β-L-deoxyribo-guanosine (β-L-dG), β-L-deoxyriboadenosine (β-L-dA) and β-L-deoxyriboinosine (β-L-dI), administered either alone or in combination, optionally in a pharmaceutically acceptable carrier. 5' and $N^4$ (cytidine) or $N^6$ (adenosine) acylated or alkylated derivatives of the active compound, or the 5'-phospholipid or 5'-ether lipids were also disclosed.

von Janta-Lipinski et al. J. Med. Chem., 1998, 41 (12), 2040-2046 disclose the use of the L-enantiomers of 3'-fluoro-modified β-2'-deoxyribonucleoside 5'-triphosphates for the inhibition of hepatitis B polymerases. Specifically, the 5'-triphosphates of 3'-deoxy-3'-fluoro-β-L-thymidine (β-L-FTTP), 2',3'-dideoxy-3'-fluoro-β-L-cytidine (β-L-FdCTP), and 2',3'-dideoxy-3'-fluoro-β-L-5-methylcytidine (β-L-FMethCTP) were disclosed as effective inhibitors of HBV DNA polymerases. In addition, von Janta-Lipinski et al. discloses the biological activity of the triphosphate of β-L-thymidine (but not β-L-2'-dC) as a nucleoside inhibitor of endogenous DNA polymerases of HBV and DHBV. However, only triphosphorylated β-L-thymidine was evaluated, not the claimed unphosphorylated form, and there is no comment in the article on whether those β-L-nucleosides are phosphorylated in cells or in vivo or, more importantly, there is no comment on the efficacy of phosphorylation of β-L-thymidine in vivo. Because of this, the article does not teach that β-L-thymidine would have any hepatitis B activity in a cell or in vivo. See also WO 96/1204.

European Patent Application No. 0 352 248 A1 to Johansson et al. discloses the use of L-ribofuranosyl compounds for the treatment of hepatitis B.

Verri et al. disclose the use of 2'-deoxy-β-L-erythro-pentofuranonucleosides as antineoplastic agents and as anti-herpetic agents (*Mol. Pharmacol.* (1997), 51(1), 132-138 and *Biochem. J.* (1997), 328(1), 317-20). Saneyoshi et al. demonstrate the use of 2'-deoxy-L-ribonucleosides as reverse transcriptase (I) inhibitors for the control of retroviruses and for the treatment of AIDS, Jpn. Kokai Tokkyo Koho JP06293645 (1994).

Giovanni et al. tested 2'-deoxy-β-L-erythro-pentofuranonucleosides against partially pseudorabies virus (PRV), *Biochem. J.* (1993), 294(2), 381-5.

Chemotherapeutic uses of 2'-deoxy-β-L-erythro-pentofuranonucleosides were studied by Tyrsted et al. (*Biochim. Biophys. Acta* (1968), 155(2), 619-22) and Bloch, et al. (*J. Med. Chem.* (1967), 10(5), 908-12).

Morris S. Zedeck et al. first disclosed β-L-dA for the inhibition of the synthesis of induced enzymes in Pseudomonas testosteroni, *Mol. Phys.* (1967), 3(4), 386-95.

In Addition, Cytosine Derivatives are useful as Intermediates for Production of Drugs such as Cytidine Diphoslphate Choline whose Generic Name is Citicoline.

Lin et al. "Synthesis of Several Pyrimidine L-Nucleoside Analogues as Potential Antiviral Agents" *Tetrahedron,* 1995, 51 (4), 1055-1068, discusses that β-L-5-iodo-2'-deoxyuridine (β-L-IUdR, compound 7) is active against herpes infection and various other DNA viruses, that BVdU and β-L-BV-ara-U are also active against herpes, β-L-BV-ara-U is active against varicella-zoster virus; and that 2',3'-dideoxy-β-L-azacytidine was found to be active against HBV.

U.S. Patent Publication No. 20030083306 filed by Idenix Pharmaceuticals, Ltd. discloses 3'-prodrugs of 2'-deoxy-β-L-nucleosides for the treatment of HBV. See also WO 01/96353.

U.S. Pat. No. 4,957,924 to Beauchamp discloses various therapeutic esters of acyclovir.

In the Apr. 17-21, 2002 European Association for the Study of the Liver meeting in Madrid, Spain, Sühnel et al. of Gilead Sciences, Inc. presented a poster indicating that combinations of adefovir with β-L-2'deoxythymidine produce additive antiviral effects against HBV in vitro.

Treatments for hepatitis B infection are also described in Lok and McMahon, AASLD Practice Guidelines, pp. 1225-1241 (2001), including treatment with interferons. Eastern woodchucks chronically infected with the woodchuck hepatitis virus (WHV) were used as a model of HBV infection to study the antiviral effect of 1-(2-fluoro-5-methyl-β-L-arabinofuranosyl)-uracil (L-FMAU) and WHV surface antigen vaccine. The humoral and cellular immunity associated with the combination of L-FMAU and vaccine resembled that observed in self-limited WHV infection. Menne et al., *J. Virology,* 76(11):5305-5314 (2002).

Synthesis of β-L-2'-Deoxy-Nucleosides

β-L-2'-Deoxynucleosides can be prepared by any number of routes. The earliest may date back to a synthesis of β-L-2'-deoxycytidine and β-L-2'-deoxythymidine by Holy, "Preparation of 2'-deoxy-L-ribonucleosides of the Pyrimidine Series", Collect. *Czech. Chem. Commun.* (1972), 37(12), 4072-87. This method involves conversion of arabinose to a pyrimidine nucleoside by a multi-step construction of the pyrimidine ring. Because this method is expensive and non-versatile, however, other methods have also been developed. One of the more versatile involves the coupling of a silylated pyrimidine or purine base to an activated deoxyribose. For this method to be successful, the deoxyribose must be activated with a good leaving group at C-1. Further, this leaving group must have the α configuration. This configuration must remain stable throughout the reaction and, in addition, the formation of the N-glycosidic bond with displacement of the leaving group must occur with inversion of the configuration thus leading to the desired β nucleoside. If these conditions are not met, the resulting product is usually a mixture of α and β nucleosides from which it is almost impossible to separate the isomers with methods other than chromatographic.

While syntheses were known for preparing β-L-2'-deoxythymidine (L-dT) in good yields, attempts at using identical syntheses to prepare L-dC were far less successful because more α-anomeric product was obtained compared to the desired β-anomer (Furukawa et al., *Chem. Pharm. Bull.,* 1968, 16:1076). In 1969 Niedballa and Vorbruggen described a process for preparing β-nucleosides by coupling a silylated N-heterocyclic compound and in particular, a pyrimidine, with a 1-O-alkyl- or preferably a 1-acyl-protected sugar such as a 1-acyl-protected ribose, deoxyribose, arabinose or glucose. The reaction utilized a Lewis acid (eg., a Friedel-Crafts catalyst) and proceeded at ambient temperatures (DE 1 919 307 to Schering Aktiengesellschaft). The process provided the β-anomeric product almost exclusively, and could work for uracil and cytosine although not as well as for thymidine (percent yields for uridine were inconsistent and ranged from 20.5%-95%; for cytidine, percent yields were 21% and 36.4%; and for thymidine, percent yields were 77% and 82.6%) (DE 1 919 307, Examples 1-10 and 12-15).

In the examples, Niedballa and Vorbruggen reported 1-O-acetyl, 1-acetyl, and 1-O-methyl ribose, deoxyribose and arabinofuranose derivative compounds as starting reagents (DE 1 919 307, Examples 1-16). It was noted that use of a 1-halo sugar as a reactant was not favored because of its instability (DE 1 919 307; JP 63026183 to Sato et al.). In the single example where a cytosine base was reacted with a 2'-deoxyribose sugar, the starting compound was 1-O-methyl-2-deoxy-3,5-toluoylribose (DE 1 919 307, Example 7, 21% yield of product).

It was surprising that the process of Niedballa and Vorbruggen formed the β-anomer to the near exclusion of the α-anomer only in the examples wherein deoxyribose and arabinose were utilized (DE 1 919 307, Examples 3 and 14). However, such results were not at all surprising where ribose or glucose was employed, because it is known that 2'-ester derivatives of ribose normally form the β-anomer in preference to the α-anomer product. Noteworthy is that where a predominance of β-anomeric product was formed from deoxyribose and/or arabinose as starting materials. Only low percent yields of product were obtained (DE 1 919 307 at Example 3, 20.5% yield from a deoxyribose starting material, and Example 14, 27.2% yield from an arabinose starting material).

In subsequent patents, Vorbruggen et al. referred to their earlier (1969) synthetic method as being "particularly disadvantageous," because the separation of the Lewis acid salts or Friedel-Crafts catalysts formed during the reaction resulted in the need for numerous, labor-intensive steps in the final work-up, and provided lower yields of the final product (DE2508312 or British equivalent GB1 542 442). In GB1 542 442, the process replacement of Lewis acids by trimethylsilyl esters of mineral acids and starting reagents that were a 1-halo, 1-O-alkyl or 1-O-acyl sugar, were reported. As before, all exemplified species utilized a 1-O-acetyl-β-D-ribofuranose starting reagent, and so, not surprisingly, produced the β-anomeric product to the near exclusion of the α-anomer (GB 1 542 442, Examples 1-13).

Likewise, in U.S. Pat. No. 4,209,613, Vorbruggen disclosed a single step nucleoside synthesis that included reacting a silylated nucleoside base with a 1-O-acyl, 1-O-alkyl or 1-halo derivative of a protected sugar in the presence of a Friedel-Crafts catalyst selected from any of a group of Lewis acids (U.S. Pat. No. 4,209,613). As before, all exemplified species utilized a 1-O-acetyl-β-D-ribofuranose starting reagent, and again, not surprisingly, produced the β-anomeric product to the near exclusion of the α-anomer (U.S. Pat. No. 4,209,613, Examples 1-16). In addition, no preference for a particular Lewis acid was given.

Vorbruggen et al., in U.S. Pat. No. 5,750,676, reported a process comprising the reaction of a free sugar with an N-heterocyclic base in the presence of a silylating agent and an inert solvent having a Lewis acid, wherein the improvement resided in the persilylation of the free sugar. The product ratios of β-anomers to α-anomers were not discussed, only D-sugars rather than L-sugars were synthesized, and no preference for a particular Lewis acid was stated. Moreover, the examples indicated that numerous preparatory steps were required in order to obtain the final products (U.S. Pat. No. 5,750,676, Examples 1-3). This would be a great disadvantage for industrial scalability.

Other processes for preparing nucleosides reported by Vorbruggen et al. include reacting a free or protected monosaccharide-trialkylsilyloxyuridine derivative compound with ammonia or a primary or secondary amine, in the presence of a tertiary amine, to form cytidine (U.S. Pat. No. 3,891,623), and a one-pot synthesis utilizing a trialkylsilyl ester of an inorganic or strong organic acid, especially a Friedel-Crafts catalyst, a nucleoside base, and a 1-O-alkyl, 1-O-acyl, or 1-halo derivative of a protected sugar derivative (U.S. Pat. No. 4,209,613).

Other attempts to convert uridine to cytidine include the following: WO 00/09531, wherein various 2'-deoxy-β-L-erythro-pentofuranonucleoside derivatives were obtained by procedures well known in the art, such as, for example, methods disclosed by Holy in *Collect. Czech. Chem. Commun.* (1972), 37(12):4072-87 and *Mol. Phys.* (1967), 3(4):386-95; and the synthesis of mono-, di-, and triphosphate derivatives of active nucleosides synthesized according to published methods for monophosphate derivatives as taught by Imai et al., *J. Org. Chem.* (1969), 34(6):1547-50, diphosphate derivatives as taught by Davisson et al., *J. Org. Chem.* (1987), 52(9):1794-1801, and triphosphate derivatives as taught by Hoard et al., *J. Am. Chem. Soc.* (1965), 87(8):1785-88.

WO 00/09531 describes the conversion of uridine derivatives to cytidine derivatives using Lawesson's reagent. Lawesson's reagent was added to a solution of 1-(3,5-di-O-benzoyl-2-deoxy-β-L-erythro-pentofuranosyl)uracil in anhydrous 1,2-dichloro-ethane and the reaction mixture was stirred under reflux for 2 hours. The solvent was then evaporated under reduced pressure and the residue was purified by silica gel column chromatography to give a 4-thio intermediate as a yellow foam. A solution of this thio intermediate (1.5 g., 3.31 mmol) in methanolic ammonia (previously saturated at −10° C. and tightly stoppered) (50 mL) was heated at 100° C. in a stainless steel bomb for 3 hours and then cooled to 0° C. The solution was evaporated under reduced pressure. The resulting crude material was purified by silica gel column chromatography (eluent: stepwise gradient of methanol (0-20%) in dichloromethane). Finally, the appropriate fractions were pooled, filtered through a unit Millex HV-4 (0.45 µm, Millipore) and evaporated under reduced pressure to provide the desired 2'-deoxy-β-L-cytidine ("β-L-dC") as a foam (0.6 g., 80%), which was crystallized from absolute EtOH.

The foregoing procedure is a derivation of the historic conversion of uridine to cytidine, published in the *J. Amer. Chem. Soc.* (1959), 81:178. Traditionally, uridine derivatives with protected hydroxyl groups in the sugar moiety were allowed to react with phosphorus pentasulfide to give 4-thio derivatives. The 4-thio derivatives then can be aminated at the 4-position with ammonia or other appropriate materials. Upon deprotection of the sugar hydroxyls, cytidine derivatives can be obtained.

Several other procedures have been proposed for converting uracil glycoside derivatives to cytidine glycoside derivatives. Vorbruggen and Niedballa in their 1982 German Patent No. DE 2122991 entitled, "Verfahren Zur Herstellung von Cytosin-Und 6-Azacytosinnucleosiden," disclosed a procedure wherein uridine or uridine derivatives that have protected hydroxyl groups were allowed to react with a silylating agent such as hexamethyldisilazane (HMDS) to give 4-O-trimethyl-silyluridine derivatives. These 4-O-trimethylsilyluridine derivatives then were aminated at the 4-position with ammonia or other appropriate material, and deprotected to produce cytidine derivatives.

A procedure for making cytidine was described in *Chem. Pharm. Bull.* (1972), 20:1050. Uridine with protected hydroxyl groups was subjected to chlorination with phosphorus oxychloride in the presence of diethylaniline hydrochloride as a catalyst, and the hydroxyl groups were deprotected, thereby providing cytidine.

GDR Pat. No. 140,254 (Official Gazette, 1980) reported a procedure wherein a uridine derivative with protected hydroxyl groups was reacted with an organic sulfonylating agent in the presence of sodium hydride to produce a 4-O-sulfonyluridine derivative. The latter derivative then was aminated at the 4-position by ammonia and deprotected to give the cytidine derivative.

U.S. Pat. No. 6,369,040 to Acevedo et al. describes the formation of pyrimidine nucleosides by nucleophilic substitution of 2,2' or 2,5'-anhydropyrimidines. Lithium enolates of acetone, methylethylketone, 2-pentanone or 2-hexanone were reacted with a 2,5'-anhydropyrimidine to yield the corresponding 2-(β-ketoalkyl)-pyrimidin-4-one deoxynucleoside.

JP 09059292 to Takeya Mori disclosed a one-pot synthesis of a 4-aminopyrimidine nucleoside from a 4-hydroxypyrimidine nucleoside by protection of the reactant's hydroxy groups with trimethylsilyl groups, subsequent reaction with phosphorus oxychloride or 4-chlorophenyl phosphorodichloridate, and amination with aqueous ammonia.

Chu reported a process for preparing 2'-deoxynucleosides that included reacting a nucleoside having 2' and 3' hydroxyl groups with a mixture of acyl bromide or acyl chloride and hydrobromic or hydrochloric acid at moderate temperatures to provide a haloacyl nucleoside derivative that was deprotected to form a desired nucleoside product (U.S. Pat. No. 5,200,514).

In Nucleosides and Nucleotides, 1996, 15(1-3):749-769, Kamaike et al. disclosed the formation of 2'-deoxyribonucleosides via nucleophilic substitution reactions of 4-azolyl-1-β-D-ribofuranosyl-pyrimidin-2(1H)-one converted from uridine with [$^{15}$N]phthalimide in the presence of triethylamine or DBU to give N$^4$-phthaloyl[4-$^{15}$N]cytidine in high yields.

Saladino et al. reported the formation of cytidine and adenosine nucleosides by dimethyldioxirane oxidation of thiopyrimidine and thiopurine nucleosides respectively, in the presence of stoichiometric amounts of amines (*J. Am. Chem. Soc., Perkin Trans.* 1 1994, 21:3053-3054).

In U.S. Pat. No. 4,689,404 to Kawada, et al., there was disclosed a process for preparing cytidine that comprised reacting $N^4,O^2$-di- or $N^4,N^4,O^2$-tri-benzoylcytosine, or a mixture of both, with 1,2,3,5-tetra-O-lower alkanoyl-β-D-ribofuranose in the presence of a Friedel-Crafts catalyst in solvent at temperatures of from 0° C. to reflux of the solvent, to obtain 2',3',5'-tri-O-lower alkanoyl-$N^4$-benzoylcytidine, and then subjecting the latter to alkali hydrolysis to provide cytidine.

JP 61263995 to Takeda Chemical Ind., Ltd., reported preparation of a cytidine nucleoside by the reaction of uridine with hexaalkyldisilazane and an acid amide in a closed vessel under pressure.

Toa Gosei Chemical Ind., Ltd., disclosed an industrially scalable synthesis of cytidine nucleosides that comprised protecting the amino group of cytosine with an n-butyryl group that was easily removed with alkali, and reacting the protected cytosine with a sugar moiety via the 3'-hydroxyl group of the sugar in the presence of a phosphoric acid-introducing agent to provide the desired, mononucleotide product. This product then was used for manufacturing oligonucleotides (JP 061359880).

In 1963, James Hunter disclosed the preparation of cytosine-1-nucleoside by acylating a uracil-1-nucleoside and reacting it with phosphorus pentasulfide to produce a fully acylated 4-thiouracil-1-nucleoside, and reacting the acylated 4-thiouracil-1-nucleoside with any basic nitrogen-containing compound that has a replaceable N-hydrogen to produce the final product (U.S. Pat. No. 3,116,282).

JP 71021872 to Sankyo Co. Ltd. describes the reaction of a silylated cytosine, uracil, thymine or azauracil base with a sugar halide, such as a halogenized ribose or glucose, in the presence of a solvent and mercuric halide.

U.S. Pat. No. 4,754,026, "Conversion of Uracil Derivatives to Cytidine Derivatives," to Mitsuru Kawada in 1988 disclosed the production of 4-O-sulfonyluridine derivatives by the reaction of uridine derivatives with protected sugar moiety hydroxyl groups with organic sulfonylating agents. When potassium carbonate was used as an acid-eliminating agent during sulfonylation, 4-O-sulfonyl derivatives were obtained nearly quantitatively. The specific action of potassium carbonate was surprising because sulfonylation did not proceed sufficiently with an alkali such as, for example, sodium carbonate as the acid-eliminating agent. However, the yield from this reaction still was low for purposes of large-scale production or when certain protecting groups were employed.

The procedures listed above are generally industrially disadvantageous because they do not produce the desired product compounds in optimal yields. In addition, certain procedures employ difficult to handle or flammable reagents such as mercuric halide or sodium hydride.

Thus, there is a need to provide an efficient, cost-effective, industrially-scalable process that favors the preparation of β-L-2'-deoxy-nucleosides over their α-anomeric stereochemical form.

SUMMARY OF THE INVENTION

An industrially-scalable synthesis is provided for nucleosides and nucleoside analogues that can produce the β-anomeric form of the desired compound in excess of the α-anomeric form in excellent yields. Also provided is a synthesis for amino-acid prodrugs of nucleoside analogues. Further provided is a method for preparing L-dC (i.e., β-L-2'-deoxycytidine) and its derivatives under mild reaction conditions.

An efficient and cost-effective procedure for synthesizing L-dC and its derivative compounds is also provided. The methods disclose herein can avoid the use of materials that are toxic, flammable, dangerous, and/or difficult to handle.

Further, provided is an efficient synthetic process for preparing 2'-deoxy-nucleosides and, in particular, amino acid-derived prodrugs of 2'-deoxy-β-L-nucleosides. This synthetic process is applicable to a wide range of nucleosides derived from various heterocyclic and heteroaromatic bases. In one embodiment, the process is directed to the synthesis of β-L-2'-deoxycytidine (LdC) and its 3'-O-valine ester prodrug form. The amino acid esters of the compounds made as described herein may be used as intermediates in the preparation of other nucleoside analogues, or may be used directly as antiviral agents.

In one embodiment, the process can include the steps of:

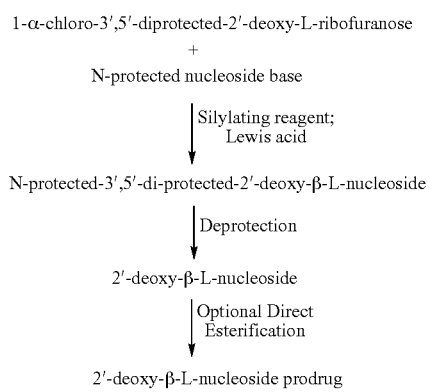

The process for direct esterification in the last step is described fully in U.S. Patent Publication No. 2004/0181051, which hereby is incorporated by reference. The process comprises reacting a 2' branched ribofuranosyl nucleoside, an optionally protected amino acid, carbonyldiimidazole and base in a one pot system, resulting in selective esterification of the 3'-hydroxyl position of the 2' branched ribofuranosyl nucleoside.

The process is advantageous in its scalability to levels for industrial production of nucleosides and nucleoside prodrugs. Moreover, its lack of labor-intensive, complicated isolation and/or purification steps suggest that it will be less costly and more efficient alternative than heretofore known in the prior art. The process can result in excellent product yields.

In one embodiment, 2'-deoxy-β-L-cytidine is prepared:

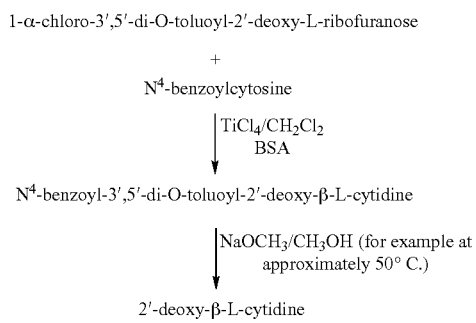

In another embodiment, 2-amino-3-methyl-butyric acid 5-(4-amino-2-oxo-2H-pyrimidin-1-yl)-2-hydroxymethyl-tetrahydro-furan-3-yl ester, or 3'-Val-O-LdC, is prepared:

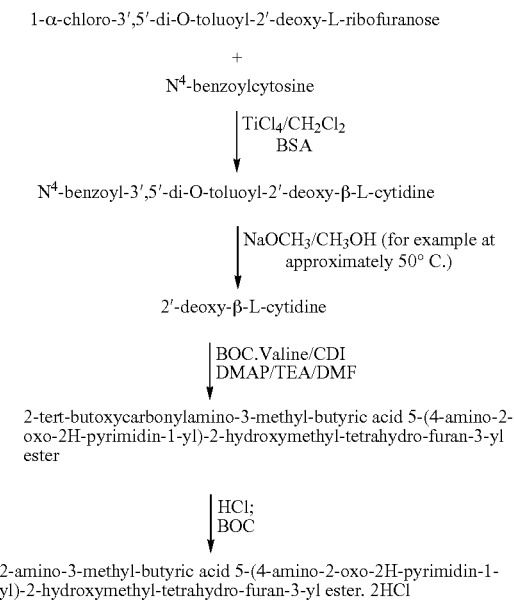

In an alternate embodiment, any natural or unnatural amino acid may be used to directly esterify the nucleoside.

In another alternate embodiment, any natural or unnatural base may replace cytosine.

Protecting groups may be selected from any of those recognized in the art as useful for protecting hydroxy and amino groups such as, for example, those taught by Greene et al., *Protective Groups in Organic Synthesis*, John Wiley and Sons, Second Edition (1991).

Likewise, any appropriate alternative reagents providing the same reaction may be used in place of those given in the embodiment(s).

In one embodiment, a process is provided for an efficient synthesis for preparing β-L-2'-deoxycytidine (L-dC) from available precursors with the option of introducing functionality or functional groups as needed. The process is applicable to a wide range of cytidine derivatives as well to nucleosides having bases other than cytosine. Moreover, the L-dC, L-dC derivatives, or nucleosides having other natural or unnatural bases made according to the present process may be used as synthetic intermediates for the preparation of a variety of other nucleoside analogues including, but not limited to, 2',3'-dideoxy and other derivatives obtained by functional group manipulations of the starting compounds.

In another embodiment, there is provided an industrially scalable process for preparing a nucleoside, nucleoside analog or a pharmaceutically acceptable salt or prodrug thereof, comprising: reacting an O-protected or N-protected natural or non-natural nucleoside base with a silylating agent, and an OH-protected halo-sugar in the presence of a Lewis acid, to form an N-protected, OH-protected β-L-nucleoside as a first product; deprotecting the first product to form a β-L-nucleoside second product; and optionally, directly esterifying the β-L-nucleoside second product with a natural or unnatural amino acid to form a β-L-nucleoside prodrug. In the process, the nucleoside base may be, e.g., adenine, guanine, thymine, cytosine, uracil, a non-natural pyrimidine, or a non-natural purine, any of which may be unsubstituted or substituted. The nucleoside base may be an $N^4$-protected cytosine. The halo-sugar may be, e.g., a halo-ribose or a halo-deoxyribose. The halo sugar may be a chloro-sugar. The halo-sugar may be a 1-α-chloro-2-deoxy-L-ribofuranose. The Lewis acid may be, e.g., a metal halide or a non-metal halide. The Lewis acid is, e.g., $SnCl_4$, $TiCl_4$, $ZnCl_2$, $AlCl_3$, CuI, $SbCl_5$, or $BF_3OEt_2$. In one preferred embodiment, the Lewis acid is $TiCl_4$. In one embodiment of the process, the protecting group is benzoyl, o-toluoyl, p-toluoyl, acetyl, acyl, alkyl, benzyl, p-methoxybenzyl ether, methoxymethyl (MOM) ether, tert-butyl dimethyl silyl (TBDMS), or tri-isopropyl silyl (TIPS). In one embodiment of the process, the silylating agent is N,O-bis-(trimethylsilyl)-acetamide (BSA) or hexamethyldisilazane (HMDS).

A solvent used in the process may be dichloromethane, dichloroethane, chloroform, tetrahydrofuran or acetonitrile, or in a particular embodiment, dichloromethane.

In a further embodiment, an industrially scalable process for preparing 2'-deoxy-β-L-cytidine or a pharmaceutically-acceptable salt or prodrug thereof is provided, comprising:

a. reacting an $N^4$-benzoylcytosine in dichloromethane with N,O-bis-(trimethylsilyl)-acetamide, to form silylated $N^4$-benzoylcytosine;

b. cooling the silylated $N^4$-benzoylcytosine in step a.;

c. adding 1-α-chloro-1,5-di-O-toluoyl-2-deoxy-L-ribofuranose to the cooled silylated $N^4$-benzoylcytosine in step b. to form a reaction mixture;

d. adding $TiCl_4$ to the silylated $N^4$-benzoylcytosine and 1-α-chloro-3,5-di-O-toluoyl-2-deoxy-L-ribofuranose reaction mixture of step c.;

e. warming the reaction mixture of step d. and allowing the reaction to run to completion;

f. quenching the reaction of step e.;

g. filtering and separating the reaction mixture from step f. to obtain an organic layer of filtrate;

h. isolating a crude 3',5'-di-O-toluoyl-2'-deoxy-β-L-cytidine product from the organic filtrate layer of step g.;

i. adding sodium methoxide in methanol to the crude 3',5'-di-O-toluoyl-2'-deoxy-β-L-cytidine product of step h.;

j. allowing the reaction mixture of step i. to run to completion to form a 2'-deoxy-β-L-cytidine product;

k. isolating the 2'-deoxy-β-L-cytidine product; and l. optionally, directly esterifying the 2'-deoxy-β-L-cytidine with an amino acid at the 3'-position to prepare a prodrug form of 2'-deoxy-β-L-cytidine.

In one embodiment of this process in step a) the reaction is run at reflux for from about 1 to 3 hours or about 2 hours. In another embodiment, in step a, the α:β anomeric ratio is at least 1:1.1 when the reaction is complete. In another embodiment, in step a, the α:β anomeric ratio is from about 1:5 to 1:6 when the reaction is complete. In one embodiment, in step b the silylated $N^4$-benzoylcytosine is cooled to a temperature of from about 0° C. to about −15° C., or about −5° C. In step e, the temperature is in one embodiment, from about 20° C. to 25° C. Optionally, in step e, the reaction goes to completion in about 2 hours. In another embodiment, in step f, the quenching reagent is saturated aqueous sodium bicarbonate. In step h, optionally the organic filtrate layer is washed with deionized water, and the solvent removed to form a product residue. The product residue is optionally dried in vacuo to provide the crude 3',5'-di-O-toluoyl-2'-deoxy-β-L-cytidine product. The crude product optionally comprises from about 70%-90% of β-anomeric product. The crude 3',5'-di-O-toluoyl-2'-deoxy-β-L-cytidine product is optionally triturated to provide its β-anomeric form. The percent yield of the β-anomeric product is optionally from about 30% to about 50%. The percent purity of the β-anomeric product is in one embodiment about 98%. In step i, the reaction may be run at about 50° C. for about 1 hour. In step j, optionally, the methanol is removed and replaced with ethanol. The trituration in ethanol optionally proceeds for about 1 hour at a temperature from about 20° C. to about 25° C. In step k, the 2'-deoxy-β-L-cytidine product isolation may include the steps of filtering, washing and drying the product in vacuo. The percent yield of 2'-deoxy-β-L-cytidine product is for example about 65% or more. The percent purity of 2'-deoxy-β-L-cytidine product is for example from about 98% to 99%. In one embodiment of the process, in step 1., the amino acid is valine.

BRIEF DESCRIPTION OF THE DRAWINGS

FIG. 3 shows the synthesis of LdC from chloro-sugar and disilylated cytosine under a variety of reaction conditions with resultant product percent yields and product α:β anomer ratios.

FIG. 5 shows the synthesis of LdC from chloro-sugar using $N^4$-benzoylcytosine.

FIG. 7 shows comparative results of coupling reactions using $N^4$-benzoylcytosine with chloro-sugar under conditions of different times, temperatures, and catalysts.

FIG. 8 shows comparative results of protected $N^4$-benzoyl-2-silylated cytosine and chloro-sugar coupling reactions where $TiCl_4$ is used as a catalyst.

DETAILED DESCRIPTION OF THE INVENTION

Figure 1:
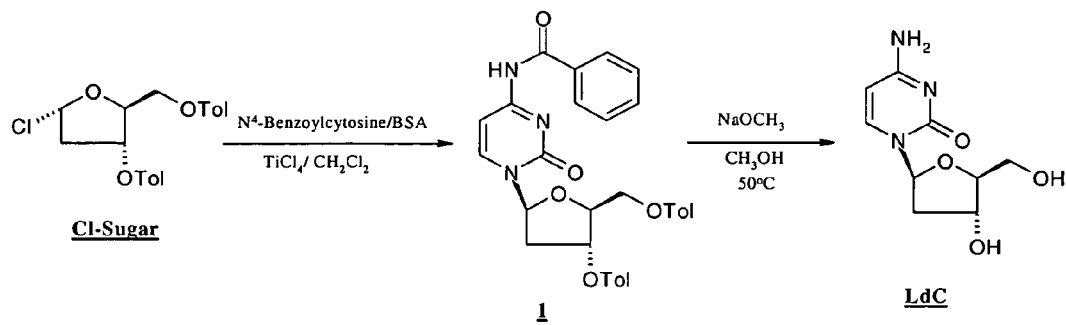
FIG. 1 is a schematic of one embodiment of a synthesis of 2'-deoxy-β-L-cytidine (β-LdC).
Figure 2:
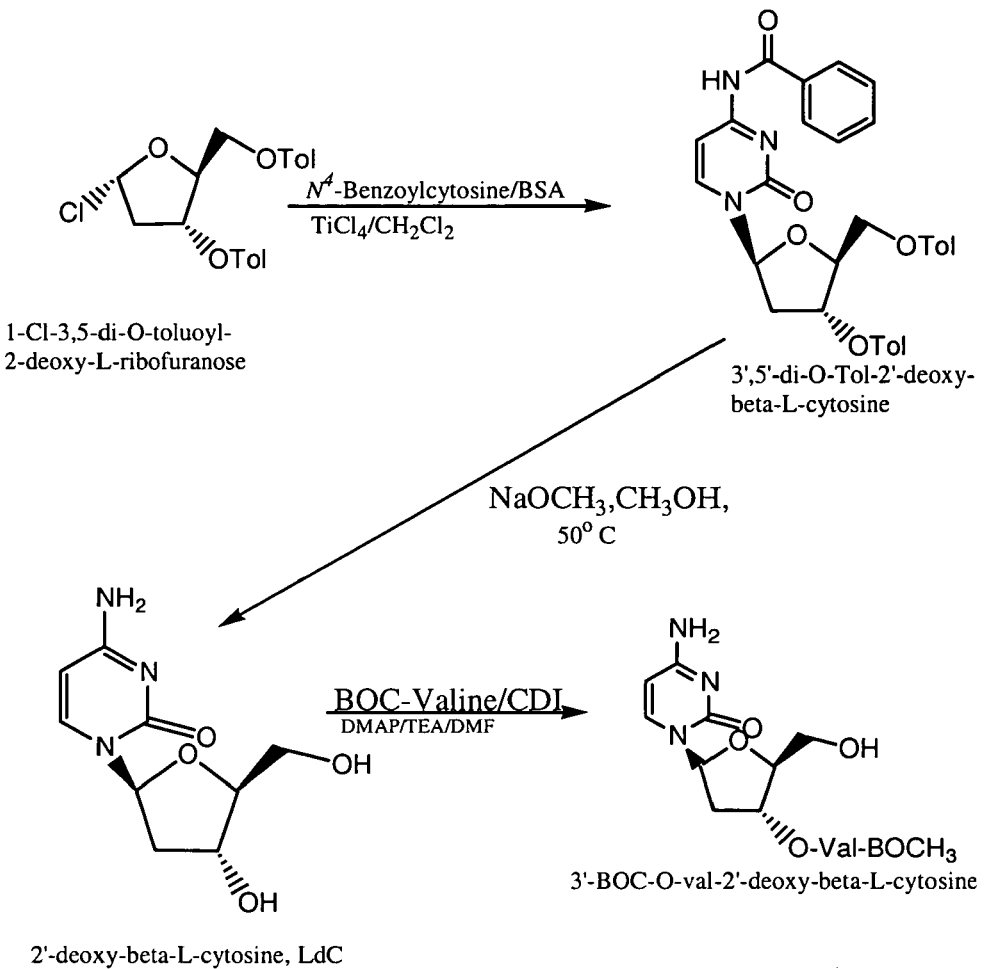
FIG. 2 is a schematic of an alternative embodiment of a synthesis of BOC 3'-O-Val-LdC.
Figure 4:
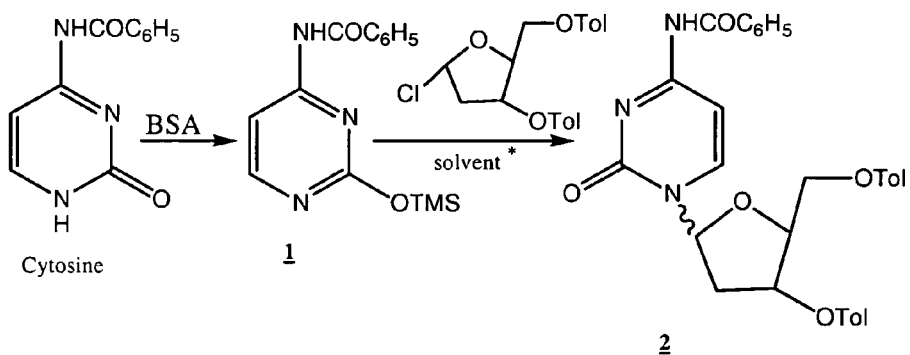
FIG. 4 shows the synthesis of LdC from chloro-sugar using silylated benzoylcytosine where no catalyst is utilized.
Figure 6:
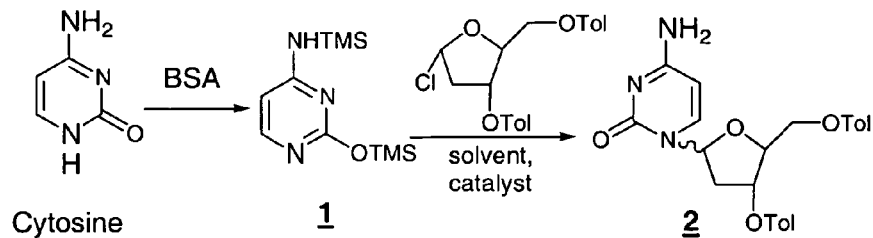
FIG. 6 compares results of coupling reactions of silylated cytosine with chloro-sugar (for example a 1-α-chloro-3,5-di-O-protected-2-deoxy-L-ribofuranose) in the presence or absence of a catalyst.
Figure 9:
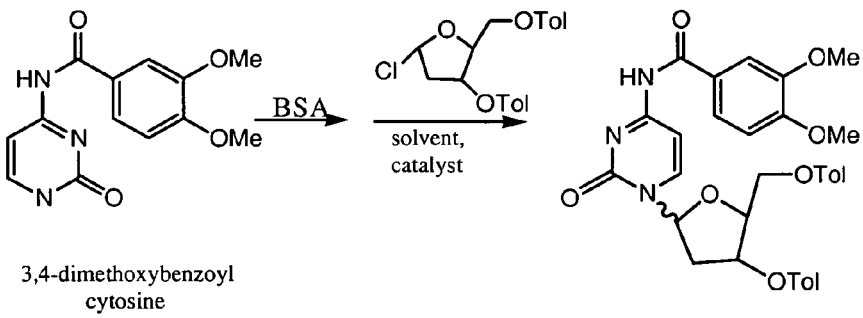
FIG. 9 shows comparative data from the use of different Lewis acid catalysts in the coupling reaction of silylated 3,4-dimethoxybenzoylcytosine and chloro-sugar.

An efficient, cost-effective, and industrially-scalable synthetic process for the formation of β-L-2'-deoxy-nucleosides, analogues, derivatives, salts and prodrugs thereof is provided. This process is applicable to a wide range of nucleoside analogues that have various heterocyclic and heteroaromatic bases. The amino acid prodrug derivatives made as described herein may be used as synthetic intermediates for the preparation of a wide range of nucleoside analogues including but not limited to α-L-2'-deoxycytidine, or may be used directly as antiviral agents.

In its generalized form, the process may include:

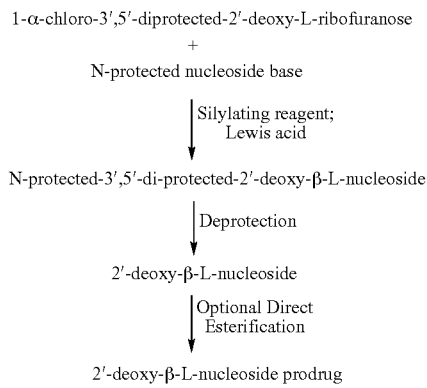

Certain combinations of temperatures and solvents can lead to decreased yields and/or to the formation of unwanted side products; therefore in a certain embodiment of the present invention the reagents and reaction conditions are selected to optimize coupling, for example by taking into account the nucleoside base being coupled to the chloro-sugar compound. For instance, the coupling reaction is exothermic. Thus, it is advisable to run this reaction at low temperatures of about −5° C. (or less) in order to obtain a nearly pure product. The selection of the solvents is important. Dichloromethane is one preferred solvent for the first step of the reaction, but it may be substituted, for example by dichloroethane or chloroform. Alternatively, tetrahydrofuran (THF) or acetonitrile may be used as a solvent in the first reaction step, but both of these solvents provide lower amounts of the desired β-isomer product.

Protecting groups for the reactants in this process are those known in the art as —OH group protectors. These include but are not limited to o-Tol, p-Tol, benzoyl, and acetyl, each of which protect the hydroxyl group by forming an ester with the —OH group; benzyl, p-methoxybenzyl ethers, and methoxymethyl (MOM), each of which forms an ether with the —OH group; and tert-butyl dimethylsilyl (TBDMS) or triisopropylsilyl (TIPS), each of which forms a silyl ether with the —OH group. In one embodiment, o-Tol is used to protect —OH groups and benzoyl is selected to protect the —NH$_2$ group on cytosine.

The reactants in the process can include a protected 1-halo sugar and an N-protected nucleoside base. Chlorine is the halogen of choice at C1 of the sugar residue. Unlike the results found in DE 1 919 307 and JP 63026183, it was found that a protected form of 1-chlororibofuranose was unstable. Instead, under the conditions described herein, 1-chlororibofuranose proved to be stable, easily handleable, and provided cytidine nucleoside in about 65% yield and approximately 99% purity. It is understood that depending upon the nucleoside base used, one or more of its positions may be protected as needed.

In the first step a silylating reagent and a Lewis acid may be used. Among Lewis acids that may be used are metal and non-metal halides, titanium tetrachloride ($TiCl_4$), tin tetrachloride ($SnCl_4$), copper iodide (CuI), aluminum trichloride ($AlCl_3$), and boron trifluoride etherate ($BF_3OEt_2$), among others. In a one embodiment, $TiCl_4$ is the Lewis acid. Both bis(trimethylsilyl)-acetamide (BSA) and hexamethyldisilazane (HMDS) may be used as silylating agents. In one embodiment, BSA is used.

Initially, the O-protected or N-protected base and the silylating reagent are mixed at a temperature from about 10° C. to 50° C., and more preferably from about 20° C. to about 25° C., or at ambient temperature. The temperature then is raised to reflux so that the reaction can run to completion, following which the mixture is cooled to from about 0° C. to −20° C., more preferably from about −5° C. to −10° C. Next the 1-halo sugar and the Friedel-Crafts catalyst are added, and the temperature of the reaction mixture is returned to ambient levels or about 20° C. for the remainder of the process. When the reaction is complete, the α:β anomeric ratio of products is about 1:5 or 1:6.

Deprotection or cleavage of the protecting groups from the nucleoside product can be accomplished by treatment with sodium methoxide in methanol or, alternatively, by other alkoxides or ammonia in alcoholic solvents.

In one embodiment, 2'-deoxy-β-L-cytidine (β-LdC) is prepared as follows:

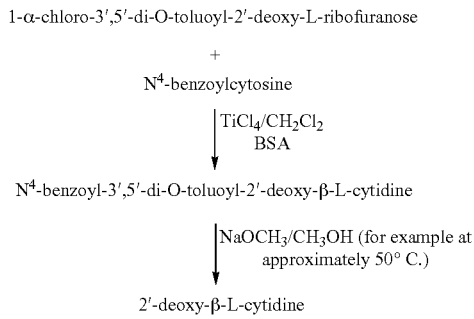

In another embodiment, 2-amino-3-methyl-butyric acid 5-(4-amino-2-oxo-2H-pyrimidin-1-yl)-2-hydroxymethyl-tetrahydro-furan-3-yl ester, the 3'-Val-O-LdC ester prodrug of LdC, is prepared, as follows:

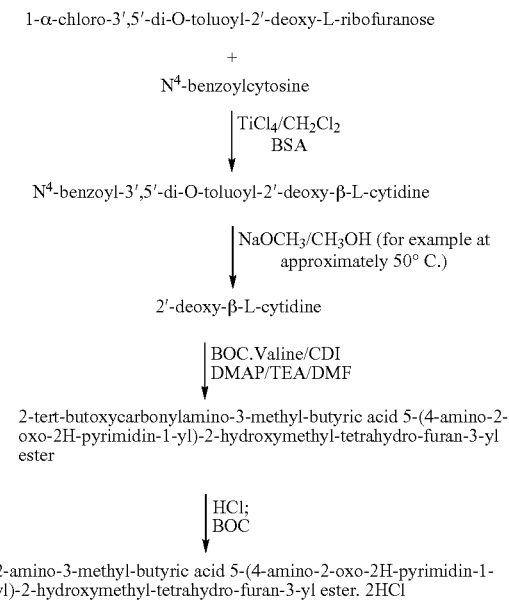

Definitions

The term "alkyl", as used herein and unless specified otherwise, includes a saturated, straight, branched, or cyclic, primary, secondary or tertiary hydrocarbon of typically $C_1$ to $C_{10}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, methylpentyl and dimethylbutyl. The term includes both substituted and unsubstituted alkyl groups. The alkyl group can be substituted by any moiety that does not adversely affect a desired property of the compound, for example with one or more positions are selected from the group consisting of halo (including fluorine, chlorine, bromine or iodine), hydroxyl, amino, alkylamino, arylamino, alkoxy, aryloxy, nitro, azido, cyano, sulfonic acid, sulfonamido, sulfate, phosphonic acid, phosphate, phosphonate, acetate or thioacetate, any or all of which may be unprotected or further protected as necessary, as known to those skilled in the art and as taught, for example, in Greene et al., *Protective Groups in Organic Synthesis*, John Wiley and Sons, $2^{nd\ Edition}$ (1991).

The terms "alkylamino" and "arylamino" include an amino group that has one or more alkyl or aryl substituents, respectively.

The terms "alkaryl" and "alkylaryl" include an alkyl group with an aryl substituent. The terms "aralkyl" and "arylalkyl" include an aryl group with an alkyl substituent.

The term "alkylene" or "alkenylene" includes a saturated divalent hydrocarbyl radical of straight or branched concfiguration, and preferably but not limited to having from one to ten carbon atoms. Non-limiting examples included within the scope of these terms are methylene, 1,2-ethane-diyl, 1,1-ethane-diyl, 1,3-propane-diyl, 1,2-propane-diyl, 1,3-butane-diyl, and 1,4-butane-diyl. The alkenylene group or other divalent moiety included here may be unsubstituted or substituted by any moiety that does not adversely affect the property of the compounds for example, with one or more moieties such as alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamoyl, ester, carboxylic acid, amide, phosphonyl, phosphinyl, phosphoryl, phosphine, thioester, thioether, acid halide, anhydride, oxime, hydrazine, carbamate, phosphonic acid, phosphonate, or other viable functional group that does not inhibit the pharmacological activity of this compound.

The term "halo" includes chloro, bromo, iodo, and fluoro.

The term "aryl" as used herein, and unless specified otherwise, includes phenyl, biphenyl or naphthyl. The term includes both substituted and unsubstituted moieties. The aryl group can be substituted by any moiety that does not adversely affect a desired property of the compounds for example, with one or more moieties such as hydroxyl, amino, alkylamino, arylamino, alkoxy, aryloxy, carboxylic acid, carboxamido, halo, acyl, aralkyl, $CF_3$, alkyl, dialkyl, alkenyl, alkynyl, cycloalkyl, bromo-vinyl, nitro, cyano, amidino, one or more 3-7-membered carbocyclic or heteroaromatic moieties optionally having one or more O, S, N or P atoms to form a heterocyclic group joined to the aryl group so as to form a spiro structure, sulfonic acid, sulfate, phosphonic acid, phosphate, or phosphonate, any of which may be further combined so as to form structurally more extensive substituents and any or all of which may be unprotected or further protected as necessary, as known to those skilled in the art and as taught, for example, in Greene et al., *Protective Groups in Organic Synthesis*, John Wiley and Sons, $2^{nd}$ Edition (1991).

The term "acyl" includes a carboxylic acid ester in which the non-carbonyl moiety of the ester group may be a straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$-$C_4$ alkyl or $C_1$-$C_4$ alkoxy, sulfonate esters such as alkyl or aralkyl sulphonyl including methanesulfonyl, the mono-, di- or tri-phosphate ester, trityl or monomethoxytrityl, substituted benzyl, trialkylsilyl such as, for example, dimethyl-t-butylsilyl or diphenylmethylsilyl. Aryl groups in the esters optimally comprise a phenyl group. The term "lower acyl" refers to an acyl group in which the non-carbonyl moiety is lower alkyl.

The term "amino acid" means any naturally-occurring or synthetic α, β, γ, or δ amino acid, of which a non-limiting list includes alanyl, valinyl, leucinyl, isoleucinyl, prolinyl, phenylalaninyl, tryptophanyl, methionyl, glycyl, serinyl, threonyl, cysteinyl, tyrosinyl, asparaginyl, glutaminyl, aspartoyl, glutaroyl, lysyl, arginyl, histidyl, β-alanyl, β-valinyl, β-leucinyl, β-isoleucinyl, β-prolinyl, β-phenylalanyl, β-tryptophanyl, β-methionyl, β-glycyl, β-serinyl, β-threonyl, β-cysteinyl, β-tyrosyl, β-asparaginyl, β-glutamyl, β-aspartoyl, β-glutaroyl, β-lysyl, β-arginyl and β-histidyl.

The terms "heteroaryl" or "heteroaromatic", as used herein, includes an aromatic compound that includes at least one sulfur, oxygen, nitrogen or phosphorus in an aromatic ring.

The term "heterocyclic" includes a nonaromatic cyclic group wherein there is at least one heteroatom such as oxygen, nitrogen, sulfur or phosphorus in a ring.

Non-limiting examples of heteroaromatic, heterocyclic, natural and non-natural bases, also referred to as nucleosides bases, that form nucleosides as disclosed herein include adenyl, guanyl, thymidinyl, cytosinyl, uracilyl, pyridyl, pyrrolopyridyl, pyrazolo-pyridyl, pyrrolo-pyrimidyl, pyrazolo-pyrimidyl, pyrimidyl, furanyl, thienyl, isothiazolyl, imidazolyl, tetrazolyl, pyridinyl, pyrimidinyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isoxazolyl, pyrrolyl, quinazolinyl, quinoxalinyl, cinnolinyl, phthalazinyl, xanthinyl, hypoxanthinyl, thiophenyl, 1,2,3-triazolyl, 1,2,4-triazolyl, tetrazolyl, pyridazinyl, pteridinyl, aziridinyl, 1,2,3-oxadiazolyl, any thiazinyl, any triazinyl, thiazinone, triazinone, piperidinyl, piperazinyl, pyrrolidinyl, oxaziridinyl, phenazinyl, phenothiazinyl, morpholinyl, thiomorpholinyl, 5-azacytidinyl, 5-azauracilyl, triazolopyridinyl, imidazolopyridinyl, pyrrolopyrimidinyl, pyrazolopyrimidinyl, benzylpurinyl, imidazopyridinyl, imidazo-pyrirnidinyl, imidazo-pyrazinyl, imidazo-pyridazinyl, imidazolidinyl, imidazolidin-diyl, pyridazinyl, triazolopyridyl, imidazolopyridyl, and imidazolotriazinyl, all of which may be unsubstituted or substituted by one or more substituent groups.

The in particular, the heteroaromatic, heterocyclic, natural and non-natural bases, also referred to as nucleosides bases, include pyrimidine and purine, base, including, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, v-alkyl-6-thiopurines, thymine, cytosine, 5-fluorocytosine, 5-methyl-cytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzyl-pyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolo-pyrimidinyl. Purine bases specifically include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl and t-butyldiphenylsilyl, trityl, alkyl groups, and acyl groups such as acetyl and propionyl, methanesulfonyl, and p-toluenesulfonyl. Alternatively, the pyrimidine, purine, heteroaromatic base, or heterocyclic base can optionally substituted such that it forms a viable prodrug, which can be cleaved in vivo. Examples of appropriate substituents include acyl moiety, an amine or cyclopropyl (e.g., 2-amino, 2,6-diamino or cyclopropyl guanosine).

The heterocyclic group optionally may be substituted by any moiety that does not adversely affect a desired property of the compounds for example with one or more moieties such as alkyl, halo, haloalkyl, hydroxyl, carboxyl, acyl, acyloxy, nitro, cyano, sulfonic acid, thiol, imine, sulfonyl, sulfanyl, sulfinyl, sulfamoyl, ester, carboxylic acid, amide, phosphonyl, phosphinyl, phosphoryl, phosphine, thioester, thioether, acid halide, anhydride, oxime, hydrazine, carbamate, carboxamide, phosphonic acid, phosphonate, or any other viable functional group that does not inhibit the pharmacologic activity of this compound, either unprotected or protected as necessary, as known to those skilled in the art, for example, as taught in Greene et al., *Protective Groups in Organic Synthesis*, John Wiley and Sons, Second Edition, 1991.

The heteroaromatic group optionally may be substituted as described above for "aryl". It may be partially hydrogenated, and any functional group that is a substituent on the heteroaromatic moiety may be protected as necessary or desired. Suitable protecting groups are well known to those skilled in the art and include, for example, trimethylsilyl, dimethylhexylsilyl, t-butyldiphenylsilyl, trityl, substituted trityl, alkyl groups, acyl groups such as acetyl and propionyl, methanesulfonyl and p-toluenesulfonyl.

The term "Lewis acid" refers to any group that is an electron acceptor and functions appropriately in the reaction described herein, such as a Friedel-Crafts catalyst. As used herein, the term "Lewis acid" and "Friedel-Crafts catalyst" embraces metal and transition metal halides such as $TiCl_4$, and non-metal halides like $BF_3$. Among the more popularly used Lewis acids are $SnCl_4$, $TiCl_4$, CuI, $ZnCl_2$, $AlCl_3$, and $SbCl_5$, and $BF_3$-etherate.

The term "protected", as used herein and unless specified otherwise, refers to a group that is added to an oxygen, nitrogen, phosphorus or other heteroatom atom to prevent its further reaction or for other purposes. A wide variety of oxygen, nitrogen and phosphorus protecting groups are known to those skilled in the art of organic synthesis, such as, for example, those groups taught in Greene et al., *Protective Groups in Organic Synthesis*, John Wiley and Sons, Second Edition, 1991.

The term amino acid includes naturally occurring and synthetic α, β γ or δ amino acids, and includes but is not limited to, alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl, and β-histidinyl.

The term "isolated" refers to a nucleoside composition that includes 85% by weight, 90% by weight, 95% by weight, 98% by weight, 100% by weight, at least 85-90% by weight, preferably 95-98% by weight, and even more preferably 99-100% by weight, of that nucleoside, with the remainder comprising other chemical species or enantiomers.

The terms "substantially free of" and/or "substantially in the absence of" as used herein refer to a nucleoside composition that includes at least 85-90% by weight, preferably 95-98% by weight, and even more preferably 99-100% by weight, of the designated enantiomer of that nucleoside. In one embodiment, the product prepared by the instant process is substantially free of enantiomers, particularly of α-anomers.

It is to be understood that all possible stereoisomers and tautomers of the groups listed above are included herein, unless it is clear from the context that a specified stereochemical configuration is intended. For example, "1-methyl-butyl" exists in both the (R) and (S) forms, and thus both (R)-1-methyl-butyl and (S)-1-methyl-butyl are covered by the term, "1-methyl-butyl" as used herein, unless otherwise specified. Some biological compounds are designated as being in the (D) or (L) form rather than the (R) or (S) form, based on the stereochemistry around the 1' and 4' carbon atoms. For example, "glycine" exists in both the (D) and the (L) forms; thus, both (D)-glycine and (L)-glycine are covered by the term "glycine" as used herein, unless otherwise specified.

The processes described herein are not limited to the use of the nucleoside base, protected sugar, or reagents exemplified. Suitable alternative reagents may be used in place of those given above. For example, p-toluoyl (p-Tol), benzoyl, acetyl, benzyl, p-methoxybenzyl, methoxymethyl (MOM), butoxycarbonyl (BOC), tert-butyl dimethylsilyl (TBDMS) or triisopropylsilyl (TIPS), or any substituted or unsubstituted silyl group, substituted or unsubstituted ether groups like C—O-aralkyl, C—O-alkyl, or C—O-aryl, substituted or unsubstituted aliphatic groups such as acyl or acetyl groups having an alkyl moiety that is straight-chained or branched, or any such groups that would not adversely affect the materials, reagents and conditions, as described, for example in Greene et al., *Protective Groups in Organic Synthesis*, John Wiley and Sons, 2$^{nd}$ Edition (1991), may be used to replace o-toluoyl (o-Tol) as an —OH protecting group. The Lewis acid $TiCl_4$ may be replaced by another Lewis acid such as, for example, tin tetrachloride ($SnCl_4$), boron trifluoride ($BF_3$), or aluminum trichloride ($AlCl_3$). Bis(trimethylsilyl)acetamide (BSA) may be replaced by hexamethyldisilazane (HMDS) as a silylating agent. The chloro group on the sugar may be replaced by any other halogen, and sodium methoxide in methanol as a deprotecting agent may be replaced by other alkoxides or ammonia in an alcoholic solvent. Likewise, while one preferred solvent is dichloromethane (DCM), other chlorinated solvents such as chloroform or dichloroethane may be used in its place, as may tetrahydrofuran (THF) and acetonitrile although the latter two solvents were found to provide lower amounts of the desired β-anomeric product.

In the optional step, TEA (triethylamine) may be replaced by diisopropylethylamine, N-ethylmorpholine, or any tertiary aliphatic amine; DMF (dimethyl formamide) may be replaced by any polar solvent such as, for example, DMSO (dimethyl sulfoxide), although DMF is one preferred embodiment based upon ease of handling and removability from the reaction mix; and CDI may be replaced by any reagent that enables coupling including, but not limited to, Mitsunobu reagents (e.g., diisopropyl azodicarboxylate and diethyl azodicarboxylate) with triphenylphosphine or carbodiimides other than carbonyl diimidazole.

This invention is further illustrated by the following non-limiting Examples. The Examples herein are set forth to aid in an understanding of the invention, are illustrative of the process and product(s) of the invention, and are not intended to and should not be interpreted to in any way limit the invention set forth in the claims that follow thereafter. For example, equivalent, similar, or suitable solvents, reagents, or reaction conditions may be substituted for those particular solvents, reagents, and/or reaction conditions described herein without departing from the spirit and scope of the invention.

EXAMPLES $^1$H NMR spectra were recorded on a Bruker 400 AMX spectrometer at 400 MHz with TMS as internal standard. Chemical shifts (δ) are reported in parts per million (ppm), and signals are reported as s (singlet), d (doublet), t (triplet), q (quartet), m (multiplet), or br s (broad singlet). TLC was performed on Uniplates (silica gel) purchased from Analtech Co. HPLC was performed with a Waters 2695 HPLC system equipped with Waters 2996 photodiode array detector and Millennium$^{32}$ software was used for system control, data acquisition and processing.

Example 1

1.A.: Synthesis of 3',5'-Di-O-toluoyl-2'-deoxy-β-L-cytidine $N^4$-Benzoylcytosine (538 mg, 2.5 mmol.) was suspended in anhydrous dichloromethane (12.5 mL) in a 25 mL 3-neck round bottom flask equipped with a reflux condenser, magnetic stirrer and an argon inlet adapter. The suspension was stirred at 20° C. under argon atmosphere and N,O-bis-(trimethylsilyl)-acetamide (0.92 mL, 3.8 mmol.) was added in one portion. The resulting mixture was stirred at reflux for 2 hours, at which time the reactants were entirely consumed. The reaction mixture was then cooled to −5° C. and 1-α-chloro-3,5-di-O-toluoyl-2-deoxy-L-ribofuranose (388.8 mg, 1.0 mmol.) was added in one portion, followed by addition of titanium (IV) chloride (1.1 mL, 10 mmol.). After 40 minutes, an aliquot of reaction mixture was removed and quenched by adding saturated aqueous sodium bicarbonate solution and extracting the aqueous layer with dichloromethane. This dichloromethane layer was analyzed by HPLC, which indicated an anomeric ratio of α:β=1:5.62. The reaction mixture was warmed to 20° C. and stirred at that temperature for 2 hours. The reaction mixture was poured into 60 mL of dichloromethane and quenched by adding saturated aqueous sodium bicarbonate solution (40 mL, pH of aqueous layer reached approximately 8.0). The mixture was filtered through a celite pad, and the celite pad was washed with dichloromethane (3×20 mL). The filtrate was transferred to a separation funnel and the layers were separated. The organic layer was washed with de-ionized water (2×20 ML) and dried over anhydrous sodium sulfate. Solvent was removed under reduced pressure and the residue obtained was dried further in vacuo to give 510 mg of crude product that contained 80.6% of the desired β-anomer as indicated by HPLC analysis. Trituration of this mixture with tert-butyl-methyl ether/acetonitrile solution (3:7, 10 mL) gave 230 mg (40%) of the desired β-isomer as an off-white solid in 98.0% purity (HPLC). This material contained only 0.7% of the α-anomer.

1.B: Synthesis of 2'-Deoxy-β-L-Cytidine (β-LdC)

Sodium methoxide (11.7 mg, 0.22 mmol.) was added to a solution of compound 1 (367.8 mg, 0.65 mmol,) in methanol (5 mL) and the reaction mixture was stirred at 50° C. After one hour, TLC (silica gel, 15% methanol in dichloromethane) indicated reaction completion. Methanol was removed under reduced pressure and ethanol (5 mL) was added. The mixture was evaporated to dryness. The residue was stirred with 3 mL of ethanol at 20° C. for one hour. The product was collected by filtration, and the filter cake washed with ethanol (2 mL), tert-butyl-methyl ether (2×3 ml) and dried in vacuo to give 96.0 mg (65%) of desired product in 98.8% purity (HPLC). $^1$H NMR (DMSO) δ ppm 8.22 and 8.00 (2 br s, 2H, $NH_2$), 7.98 (d, 1H, H-6, J=7.59 Hz), 6.12 (t, 1H, H-1', J=6.5 Hz and J=7.6 Hz), 5.89 (d, 1H, H-5, J=7.59 Hz), 5.3 (br s, 1H, OH-3'), 5.1 (br s, 1H, OH-5'), 4.2 (m, 1H, H-3'), 3,80 (q, 1H, H-4', J=3.6 Hz and J=6.9 Hz), 3.6-3.5 (m, 2H, H-5', H-5''), 2.2-2.0 (m, 2H, H-2', H-2'').

We claim:

1. An industrially scalable process for preparing a mixture of α-L-2'-deoxycytidine and β-L-2'-deoxycytidine or a mixture of α-L-thymidine and β-L-thymidine or a pharmaceutically acceptable salt thereof, comprising the steps of:
   (a) reacting an N- and/or O-protected cytosine or thymine with a silylating reagent at a temperature from about 10° C. to 50° C., or at ambient temperature, optionally in the presence of a catalyst, to form a silylated cytosine or thymine;
   (b) raising the temperature to reflux in order to run the reaction to completion;
   (c) cooling the mixture of (a) to about 0° C. to −20° C.;
   (d) reacting the silylated cytosine or thymine with a protected 1-halo-2-deoxy-L-sugar in the presence of a Lewis acid at a temperature of about 20° C. to form an N- and/or O-protected deoxycytidine or thymidine mixture;
   (e) reacting the N- and/or O-protected deoxycytidine or thymidine anomeric mixture with a deprotecting reagent, to form a mixture of α-L-2'-deoxycytidine and β-L-2'-deoxycytidine or a mixture of α-L-thymidine and β-L-thymidine,
wherein the Lewis acid is selected from $SnCl_4$, $TiCl_4$, $AlCl_3$, $ZnCl_2$, CuI, $SbCl_5$, and $BF_3(OEt_2)$, wherein said sugar moiety is a protected 2-deoxy-1-L-ribofuranosyl moiety, and wherein the predominate product in each product mixture is the β anomer.

2. The process of claim 1 wherein the final nucleoside product has an α:β anomeric ratio of about 1:5 to 1:6.

3. The process of claim 1 wherein the 1-halo-2-deoxy-L-sugar is a 1-chloro-2-deoxy-L-ribose.

4. The process of claim 1 wherein the 1-halo-2-deoxy-L-sugar is an α-1-halo-2-deoxy-L-ribose.

5. The process of claim 4 wherein the α-1-halo-2-deoxy-L-sugar is an α-1-chloro-2-deoxy-L-ribose.

6. The process of claim 1 wherein the Lewis acid is a Friedel-Crafts catalyst.

7. The process of claim 1 wherein the deprotecting reagent is an alkoxide or ammonia in an alcoholic solvent.

8. An industrially scalable process for preparing a mixture of 2'-deoxy-α-L-cytidine and 2'-deoxy-β-L-cytidine or a pharmaceutically-acceptable salt thereof, comprising the steps of:
   (a) reacting an $N^4$-protected cytosine with a silylating reagent, optionally in the presence of a catalyst, to form a silylated cytosine;
   (b) reacting the silylated cytosine with a protected 1-halo-2-deoxy-L-ribofuranose in the presence of a Lewis acid to form a mixture of $N^4$-protected 2'-deoxy-α-L-cytidine and $N^4$-protected 2'-deoxy-β-L-cytidine; and
   (c) reacting the $N^4$-protected 2'-deoxy-α-L-cytidine and $N^4$-protected 2'-deoxy-β-L-cytidine mixture with a deprotecting reagent, to form a mixture of 2'-deoxy-α-L-cytidine and 2'-deoxy-β-L-cytidine, wherein the coupling reaction of step (b) is performed at a temperature of about −5° C. or less,
wherein the Lewis acid is selected from $SnCl_4$, $TiCl_4$, $AlCl_3$, $ZnCl_2$, CuI, $SbCl_5$, and $BF_3(OEt_2)$ and wherein the predominate product in the product mixture is the β anomer.

9. The process of claim 8 wherein the final nucleoside product has an α:β anomeric ratio of about 1:5 to 1:6.

10. The process of claim 8 wherein the 1-halo-2-deoxy-L-ribofuranose is a 1-chloro-2-deoxy-L-ribofuranose.

11. The process of claim 8 wherein the 1-halo-2-deoxy-L-ribofuranose is an α1-halo-2-deoxy-L-ribofuranose.

12. The process of claim 11 wherein the α-1-halo-2-deoxy-L-ribofuranose is an α-1-chloro-2-deoxy-L-ribofuranose.

13. The process of claim 8 wherein the Lewis acid is a Friedel-Crafts catalyst.

14. The process of claim 13 wherein the Friedel-Crafts catalyst is $TiCl_4$.

15. The process of claim 8 further comprising directly esterifying 2'-deoxy-α-L-cytidine and/or 2'-deoxy-β-L-cytidine with an amino acid at the 3'-position in the presence of a polar aprotic solvent and a coupling agent selected from the group consisting of EDC (1-[3-(dimethylamino)-propyl]-3-ethyl-carbodiimide hydroxide), carbonyldiimidazole (CDI), BOP reagent (benzotriazol-1-yloxy-tris(dimethylamino)-phosphonium hexafluorophosphate, and diethyl azodicarboxylate in the presence of triphenylphosphine (Mitsunobu reaction), to prepare a 3'-ester of 2'-deoxy-α-L-cytidine and/or 2'-deoxy-β-L-cytidine.

16. An industrially scalable process for preparing a mixture of 2'-deoxy-α-L-cytidine and 2'-deoxy-β-L-cytidine or a pharmaceutically-acceptable salt thereof, comprising the steps of:
   (a) reacting an $N^4$-benzoylcytosine with a silylating agent, to form silylated $N^4$-benzoylcytosine;
   (b) adding 1-α-chloro-3',5'-di-O-toluoyl-2'-deoxy-L-ribofuranose, in the presence of a Lewis acid, to the silylated $N^4$-benzoylcytosine to form a mixture of 3',5'-di-O-toluoyl-2'-deoxy-α-L- and 3',5'-di-O-toluoyl-2'-deoxy-β-L-cytidines; and
   (c) deprotecting the mixture of 3',5'-di-O-toluoyl-2'-deoxy-αL-cytidine and 3',5'-di-O-toluoyl-2'-deoxy-β-L-cytidine, wherein the coupling reaction of step (b) is performed at a temperature of about −5° C or less,
wherein the Lewis acid is selected from $SnCl_4$, $TiCl_4$, $AlCl_3$, $ZnCl_2$, CuI, $SbCl_5$, and $BF_3(OEt_2)$ and wherein the predominate product in the product mixture is the β anomer.

17. The process of claim 16 wherein the final nucleoside product has an α:β anomeric ratio of about 1:5 to 1:6.

18. The process of claim 16 wherein the silylating agent is N,O-bis-(trimethylsilyl)-acetamide.

19. The process of claim 16 wherein the Lewis acid is a Friedel-Crafts catalyst.

20. The process of claim 19 wherein the Friedel-Crafts catalyst is $TiCl_4$.

21. The process of claim 16 wherein the reaction is run in dichloromethane.

22. The process of claim 16 wherein the 3',5'-di-O-toluoyl-2'-deoxy-β-L-cytidine is deprotected by using sodium methoxide in methanol.

23. The process of claim 16 further comprising directly esterifying 2'-deoxy-α-L-cytidine and/or 2'-deoxy-β-L-cytidine with an amino acid at the 3'-position in the presence of a polar aprotic solvent and a coupling agent selected from the group consisting of EDC (1-[3-(dimethylamino)-propyl]-3-ethyl-carbodiimide hydroxide), carbonyldiimidazole (CDI), BOP reagent (benzotriazol-1 -yloxy-tris(dimethylamino)-phosphonium hexafluorophosphate, and diethyl azodicarboxylate in the presence of triphenylphosphine (Mitsunobu reaction), to prepare a 3'-ester of 2'-deoxy-α-L-cytidine and/or 2'-deoxy-β-L-cytidine.

* * * * *